(12) United States Patent
Pittaccio et al.

(10) Patent No.: US 9,314,391 B2
(45) Date of Patent: Apr. 19, 2016

(54) JOINT FOR ARTICULATIONS WITH PSEUDO-ELASTIC ELEMENTS

(75) Inventors: Simone Pittaccio, Milan (IT); Stefano Viscuso, Cavallasca-Como (IT); Stefano Besseghini, Tirano-Sondrio (IT)

(73) Assignee: CONSIGLIO NAZIONALE DELLE RICERCHE (IT)

( * ) Notice: Subject to any disclaimer, the term of this patent is extended or adjusted under 35 U.S.C. 154(b) by 321 days.

(21) Appl. No.: 13/696,134

(22) PCT Filed: May 2, 2011

(86) PCT No.: PCT/EP2011/002184
§ 371 (c)(1),
(2), (4) Date: Nov. 5, 2012

(87) PCT Pub. No.: WO2011/137999
PCT Pub. Date: Nov. 10, 2011

(65) Prior Publication Data
US 2013/0053741 A1 Feb. 28, 2013

(30) Foreign Application Priority Data
May 5, 2010 (IT) .............. MI2010A0784

(51) Int. Cl.
*A61F 5/01* (2006.01)
*A61H 1/02* (2006.01)
(Continued)

(52) U.S. Cl.
CPC .............. *A61H 1/024* (2013.01); *A61F 5/0102* (2013.01); *A61F 5/013* (2013.01); *A61F 5/0127* (2013.01);
(Continued)

(58) Field of Classification Search
CPC ............... A63B 23/1281; A63B 23/14; A63B 21/4017; A63B 21/4019; A63B 21/4021; A63B 21/4011; A63B 21/4013; A63B 21/4015; A61F 5/0123; A61F 5/0125; A61F 5/0127; A61F 5/013; A61F 2005/0179; A61F 2005/0197; A61H 1/024; A61H 1/0266; A61H 1/0274; A61H 1/0277; A61H 1/0285; Y10T 16/53828; Y10T 16/53845; Y10T 16/5384
USPC ..................... 602/12, 16, 20, 23, 26; 482/121
See application file for complete search history.

(56) References Cited

U.S. PATENT DOCUMENTS 4,433,679 A * 2/1984 Mauldin et al. ................. 602/16
4,665,905 A 5/1987 Brown
(Continued)

FOREIGN PATENT DOCUMENTS

CH 347467 A 6/1960
WO WO2009076725 A1 6/2009

OTHER PUBLICATIONS

International Search Report July 15, 2011.

*Primary Examiner* — Victoria J Hicks
*Assistant Examiner* — Kari Petrik
(74) *Attorney, Agent, or Firm* — Timothy J. Klima; Shuttleworth & Ingersoll, PLC

(57) ABSTRACT

A joint for articulations with pseudo-elastic elements comprising a pair of coupled box-shaped elements (13, 14), facing each other in an open surface, moveable and rotating with respect to each other, around a common longitudinal axis (15) and containing a spring-charged pseudo-elastic element (12) which causes the reciprocal rotation, the box-shaped elements (13, 14) carrying an arm (20, 25) facing outwardly for connection with associated portions of an articulation and including stop elements (21, 32; 132, 20) of their rotation. The spring-charged pseudo-elastic element (12) comprises a curved portion, more or less closed to form a ring (36) and two straight portions (37) terminating in ends (23, 34), inserted into holes (22, 33) of the box-shaped elements (13, 14), the straight portions (37) being intersected to obtain a pre-charge before being inserted into the holes (22, 33).

11 Claims, 4 Drawing Sheets

(51) Int. Cl.
*A63B 21/02* (2006.01)
*A63B 21/00* (2006.01)
*A63B 23/04* (2006.01)
*A63B 23/08* (2006.01)
*A63B 23/12* (2006.01)
*A63B 23/14* (2006.01)

(52) U.S. Cl.
CPC ............ *A61H 1/0266* (2013.01); *A61H 1/0277* (2013.01); *A61H 1/0285* (2013.01); *A63B 21/025* (2013.01); *A63B 21/4013* (2015.10); *A63B 21/4025* (2015.10); *A63B 21/4047* (2015.10); *A61F 2005/0179* (2013.01); *A61F 2005/0197* (2013.01); *A63B 21/00069* (2013.01); *A63B 21/4017* (2015.10); *A63B 23/0494* (2013.01); *A63B 23/08* (2013.01); *A63B 23/1281* (2013.01); *A63B 23/14* (2013.01); *Y10T 403/32557* (2015.01)

(56) References Cited

U.S. PATENT DOCUMENTS

| | | |
|---|---|---|
| 5,337,737 A | 8/1994 | Rubin et al. |
| 5,685,830 A | 11/1997 | Bonutti |
| 5,891,061 A | 4/1999 | Kaiser |
| 6,001,075 A | 12/1999 | Clemens et al. |
| 6,718,656 B2 | 4/2004 | Houser et al. |
| 6,736,766 B1 * | 5/2004 | Gallant .................. 482/114 |
| 6,936,020 B2 | 8/2005 | Davis |
| 7,033,330 B2 | 4/2006 | de Lint |
| 7,601,130 B2 | 10/2009 | Farrell et al. |
| 2009/0042701 A1 * | 2/2009 | Tsai ..................... 482/121 |

* cited by examiner

JOINT FOR ARTICULATIONS WITH PSEUDO-ELASTIC ELEMENTS

The present invention relates to a joint for articulations with pseudo-elastic elements.

Various techniques and arrangements are used in the field of articulations for obtaining a good functionality of the limb for which they are envisaged. The application of a force for extending a contracted limb and restoring its functioning has already been proposed, for example.

In particular, some patents envisage the use of elastic elements which connect the plastic valves of the orthosis (U.S. Pat. No. 4,665,905 and U.S. Pat. No. 7,033,330); others propose joints or more complex mechanisms for obtaining the same objective (U.S. Pat. No. 5,337,737; U.S. Pat. No. 5,685,830; U.S. Pat. No. 5,891,061; U.S. Pat. No. 6,001,075; U.S. Pat. No. 6,936,020; and U.S. Pat. No. 7,601,130).

The use of pseudo-elastic elements in an orthosis is, on the other hand, a relatively new application. U.S. Pat. No. 6,718,656 of Houser has proposed the use of pseudo-elastic elements inserted in shoes for improving sports performances and holding and stabilizing the ankle. Houser also suggests uses for other articulations for rehabilitation or physical exercise, but only one drawing (extremely schematic) referring to the knee is proposed for these applications, which does not explain this application.

U.S. Pat. No. 7,033,330 of de Lint proposes an orthosis for the wrist which assembles pseudo-elastic elements. The device is optimized for relaxing the extensor muscles of the wrist and is designed so that the two shells of the orthosis are connected either laterally to the wrist by bars of superelastic material or at the back by a band containing superelastic material. In both cases, no system is envisaged for keeping the pseudo-elastic elements pre-charged. This solution can be good for the orthosis of de Lint as the objective to be reached is to alleviate muscular pain not linked to neurological damage. The orthosis of de Lint, in fact, aims at helping the extensor muscles of the wrist to maintain a neutral position of the articulation. For patients who have undergone neurological damage, this type of approach is not suitable for bringing the articulation to the desired position, as a spastic or contracted muscle can require more extensive forces. Furthermore, with respect to the wrist, an ample portion of movement is available in addition to the neutral position (hyperextension) and from a therapeutic point of view it may be appropriate to also reach these angular positions. This is possible on the condition that there is a sufficient pre-charging on the pseudo-elastic elements, which is not envisaged by de Lint. It should also be noted that in the solution of de Lint, the superelastic element is not contained in any protective casing and its possible breakage could injure the patient.

In spite of these known solutions, it should be pointed out that following neurological damage, vicious circles are established which, within a few weeks, lead to the formation of muscular contractures which generally limit the functionality of the limbs.

The simultaneous development of spasticity produces an excessive reflex response to the mobilization of the articular segments involved.

Traditionally, therapeutic repositioning is sought through the administration of orthoses which firmly constrain the articulations in positions which gradually approach the clinical objective. This process takes place with discreet steps and each variation in the angle creates discomfort for the patient which lasts until the mobilized muscle is remodelled to adapt itself to the new length imposed. During this process, the limb therefore remains immobilized and unused and residual voluntary movements or reflexes are also prevented.

The technical problem to be solved for overcoming the immobility and disuse inherent in the traditional techniques is to guarantee a dynamic repositioning through the imposition of a corrective force instead of a forced elongation. As it is important for this force to be present and to be as uniform as possible throughout the whole articular excursion covered during the repositioning, all elastic systems which induce excessively high forces at the beginning of the repositioning and excessively low forces when approaching the final desired position, must be discarded.

There are solutions in which the pretensioning of the elastic elements can be varied during the therapy to maintain a constant action, but this is not practical due to the necessity of a supervision or the risk of undesired manipulations of the therapeutic scheme on the part of the patient.

An objective of the present invention is to find a solution or a device capable of providing almost constant forces throughout the whole movement span of interest.

This would in fact eliminate both problems relating to variations or discrepancies in the therapeutic intensity with respect to the recovery course, and also the necessity for applying continuous corrections to the parameters of the device.

A further objective to be reached is to have a better interfacing with the daily oscillations in the neuromuscular conditions of the patient which overlap with the more regular recovery curve.

A further problem to be solved is that in many patients the existence of active movements (especially un-controlled) together with the paresis lead to a problem of interfacing with the traditional rigid ortheses, as with each involuntary contraction a strong pressure can be exchanged at the skin-brace interface.

In short, a general objective of the present invention is to solve the drawbacks of the known art mentioned above in an extremely simple, economical and particularly functional manner.

In view of the above objectives, according to the present invention, a joint for articulations with pseudo-elastic elements has been conceived, having the characteristics specified in the enclosed claims.

The structural and functional characteristics of the present invention and its advantages with respect to the known art will appear even more evident from the following description, referring to the enclosed drawings, which, among other things, show embodiments of a joint for articulations with pseudo-elastic elements produced according to the present invention.

With reference to the figures, these illustrate the conformation and use of joints for articulations with pseudo-elastic elements produced according to the present invention.

Figure 1:
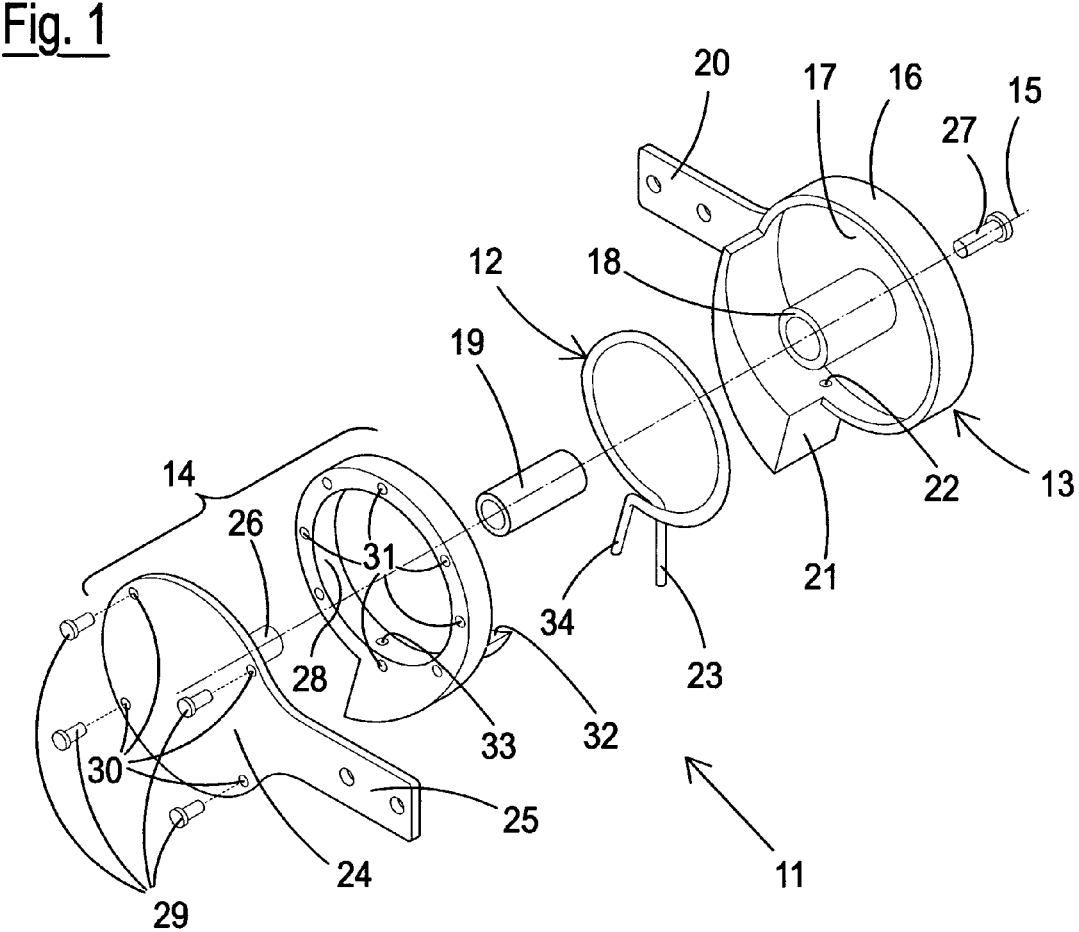
FIG. 1 is an exploded schematic perspective view of an embodiment of a joint according to the present invention.

FIG. 1 shows a first embodiment of a joint 11 for articulations with a pseudo-elastic element 12 inserted therein.

More specifically, the joint 11 comprises a pair of coupled box-shaped elements 13 and 14, facing each other in the open surface, moveable and rotating with respect to each other, around a common longitudinal axis 15 and containing the spring-charged pseudo-elastic element 12 which causes their reciprocal rotation.

In the example of FIG. 1, the first box-shaped element 13 comprises a closed hollow cylindrical body 16 in correspondence with a base 17. A sleeve 18 is positioned on the base 17, centrally and aligned with the axis 15, which acts as an external housing for a bearing 19, for example a ball bearing.

Figure 1A:
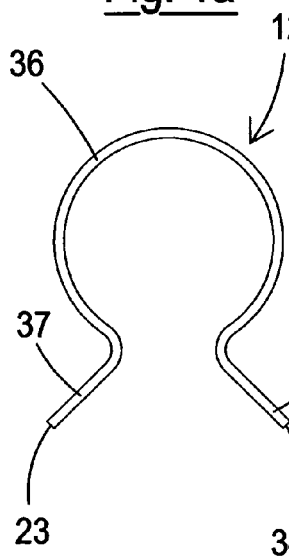
FIGS. 1a, 1b and 1c show a pseudo-elastic element in rest, semi-charged and completely charged position of insertion in the joint.
Figure 1B:
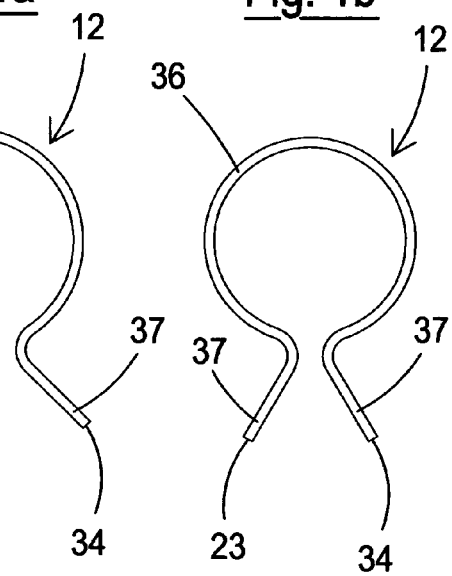

A first arm 20, positioned on the outer surface of the base 17, extends radially and outwardly from the hollow body 16. Furthermore, from the opposite part of the hollow body 16, a first shaped stop-surface 21 extends radially towards the outside and axially towards the second box-shaped element 14. A hole 22 is envisaged inside the hollow body 16 or in any case from the first box-shaped element 13, for housing a first end 23 of the pseudo-elastic element 12, in the form of a wire spring also shown in FIGS. 1a-1c which will be described further on.

The second box-shaped element 14 comprises a circular plate 24 equipped with a second arm 25 positioned radially towards the outside. A cylindrical pin 26 extends from the centre of the circular plate 24 in the direction of the axis 15, towards the first box-shaped element 13, which acts as an internal seat for the bearing 19 and is suitable for being inserted therein and receiving a fixing screw 27 in a coupling position of the box-shaped element 13, 14 keeping the joint 11 closed.

The sleeve 18 and the pin 26 act as extensions of the two box-shaped elements 13, 14 and the screw 27 acts as an axial constraining means of these, leaving the reciprocal rotation free.

A circular annular element 28 can be constrained to the circular plate 24 by means of screws 29 at least partially passing into holes 30 of the circular plate 24 and which are screwed inside threaded holes 31 of the circular annular element 28. In particular, in FIG. 1 there are four holes 30 and eight holes 31 for allowing a fixing of the plate 24 and annular element 28 in two different reciprocal positions. In other embodiments, the holes 30, 31 and the positions can be in a greater number to allow use with different movement excursions and with different pre-charges of the pseudo-elastic element 12.

A second shaped stop-surface 32 also extends radially from the annular element 28, towards the outside and axially towards the first box-shaped element 13, which is shaped so as to be able to be buffered against the first shaped stop-surface 21 of the first box-shaped element 13.

The first shaped stop-surface 21 of the first box-shaped element 13 and the second shaped stop-surface 32 of the annular element 28 of the second box-shaped element 14 create a mechanical block and act as stop elements thus creating a run-end position for the joint, or for the orthesis to which it is applied.

Finally, a hole 33 is envisaged in the annular element 28 of the second box-shaped element 14 thus formed, for housing a second end 34 of the pseudo-elastic element 12.

Figure 1C:
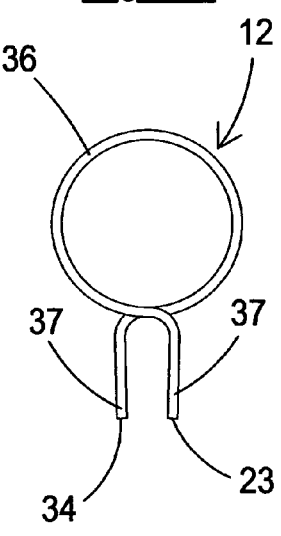

The ends 23 and 34 of the pseudo-elastic element 12 are inserted in the holes 22 and 33 of the first box-shaped element 13 and annular element 28 of the second box-shaped element 14 before closing the joint 11 in the position as shown in FIG. 1c or in FIG. 1.

Figure 2:
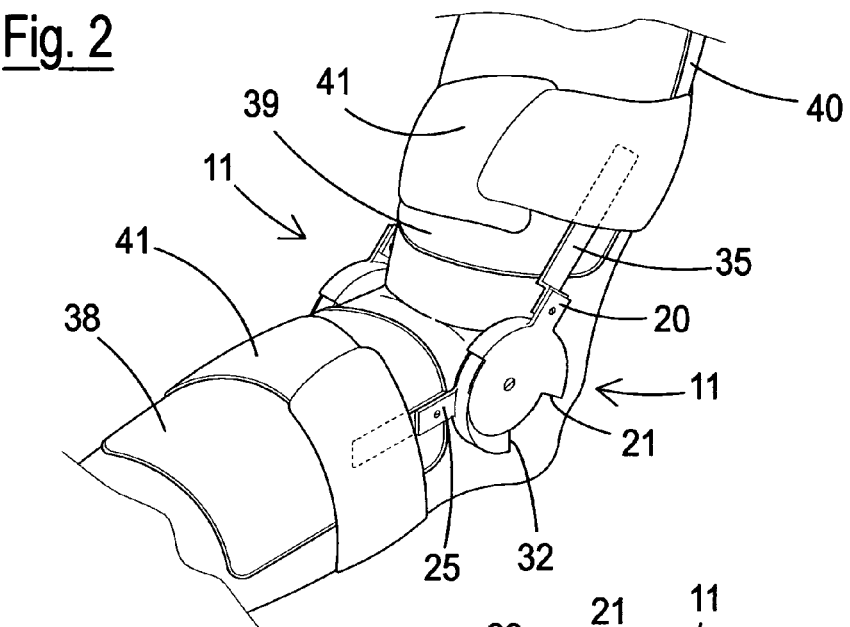
FIG. 2 is a schematic perspective view which illustrates the use of a pair of joints of FIG. 1 applied to an orthesis for the extension of the elbow.
Figure 3A:
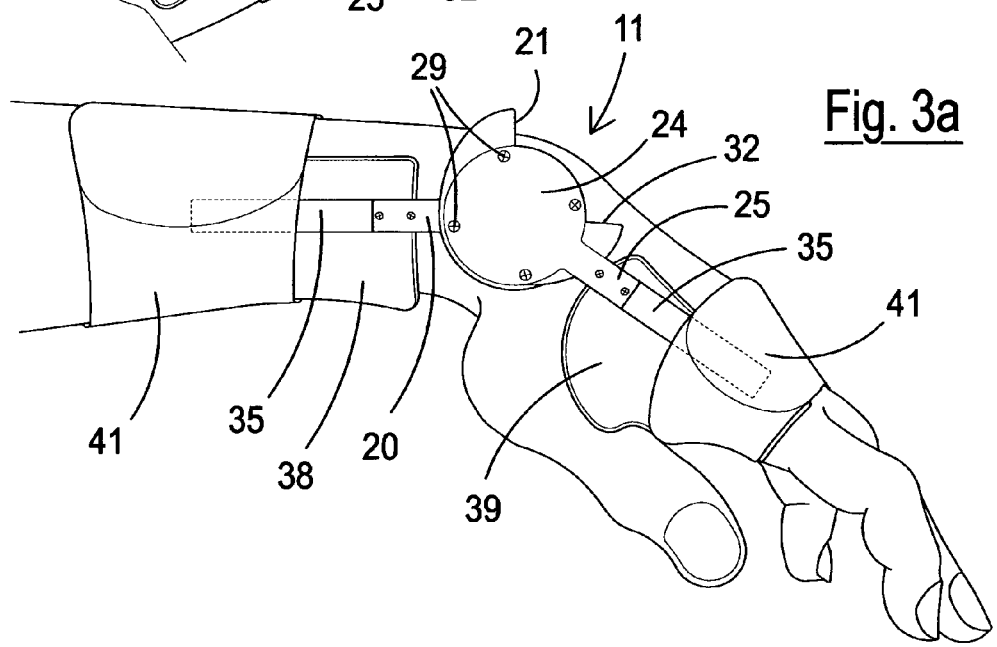
FIGS. 3a and 3b are schematic perspective views which illustrate the use of joints of FIG. 1 applied for wrist ortheses.
Figure 3B:
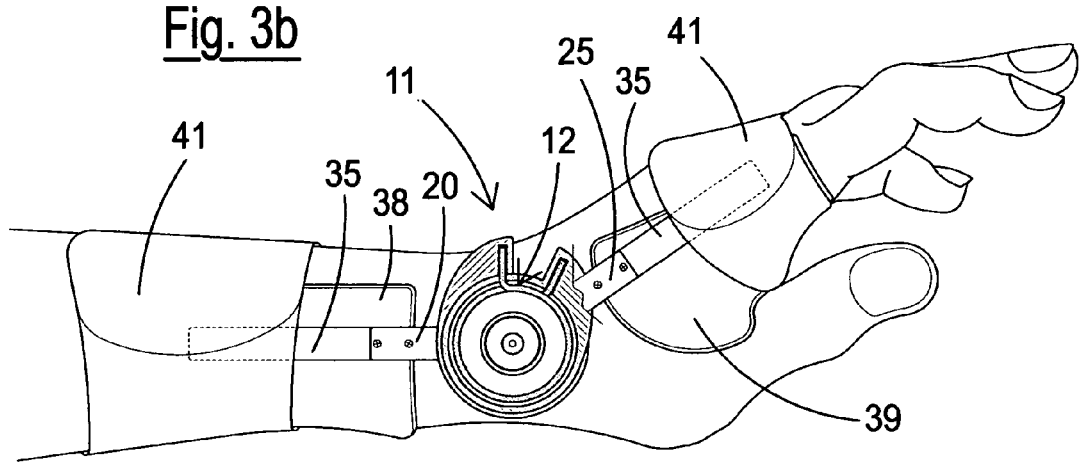

It can be seen how the first box-shaped element 13 and the second box-shaped element 14 each have an arm 20, whereby it is possible to connect the joint to the rest of the orthesis, as shown in FIGS. 2, 3a, 3b also by means of connection bars 35, or in any case to two articulated rods or portions associated with an articulation.

With respect to the pseudo-elastic element 12, it can be seen how, in the joint of the present invention, this is produced by a spring (made of pseudo-elastic material) composed of a curved portion which is more or less closed to form a ring 36 and two straight portions 37 terminating in ends 23 and 34. The form proposed has been studied to obtain uniform stress of the material along the curved portion of the spring. The straight portions 37 are intersected to obtain a pre-charge before being inserted into the holes 22 and 33.

When a spring with the form proposed is pre-charged as described, it tends to leave the plane in which it was formed and the presence of a joint also serves to limit the encumbrance outside the forming plane and prevent the spring from coming into contact with the patient's skin creating rubefactions or releasing undesired forces.

The pseudo-elastic material is a wire having a circular section with a diameter ranging from 1 mm to 3 mm, or with a different section but suitable for producing comparable forces. It should be pointed out that the use of wires with different diameters (or dimensions) implies minimum measurement variations in the design of the joint. The preferred material for the application is NiTi, but other pseudo-elastic alloys based on NiTi (comprising but not limited to NiTiCr), or other superelastic alloys or other materials with pseudo-elastic or hyperelastic characteristics, can be used. The preferred thermo-mechanical treatment in the preparation of the pseudo-elastic alloy comprises mechanical strain-hardening from 20% to 70%, cold forming into the configuration described with the use of suitable instruments, comprising but not limited to templates, matrixes or constraints, and oven aging for registering the form. The preferred aging is at a temperature ranging from 350° C. to 550° C. for a time ranging from 10 minutes to 1 hour followed by rapid cooling (in water or ice or oil or other means). The forming and treatment can be divided into two or more phases to obtain desired forms and characteristics. Temperatures and treatment times can be outside the preferred range in relation to special applications (for example low forces required for pediatric patients). In addition to oven treatment, localized treatment can be adopted, especially but not exclusively, for obtaining the desired curvatures.

FIG. 2 is a schematic perspective view which illustrates the use of a pair of joints of FIG. 1 applied to an orthesis for the extension of an elbow.

The orthesis is composed of two valves or shells made of a thermoplastic material 38 and 39 connected to the patient's arm 40 by means of Velcro strips 41.

The joints 11, one per part, are connected to these valves 38 and 39 by means of the connection bars 35 which can be shaped for taking the anatomic encumbrances into account. The bars 35 are fixed to the joint 11 and valves 28, 39 by means of screws or rivets (not shown). In the example, two joints 11 are positioned on the elbow, care being taken that the rotation axes of the two joints coincide as much as possible with the rotation axis of the articulation corresponding to the degree of articular freedom for which rehabilitation is to be obtained.

FIGS. 3a and 3b are views which illustrate the use of joints 11 of FIG. 1 applied for wrist ortheses.

Analogously to the case of the elbow, two thermoplastic valves 38 and 39 are connected to the forearm and hand by means of Velcro strips 41. Connection bars 35 are screwed or riveted to both the valves 38, 39 and to the joints 11 and can have a suitably shaped form. The spring pseudo-elastic element 12 inserted in the inner chamber of the joint 11 thus transfers its recovery force to the valves 38, 39, as can be clearly seen in FIG. 3b which is partially sectional.

In the wrist orthosis with pseudo-elastic joints 11, the spastic contraction of the flexor muscles of the hand ensures that, at the beginning of the therapy, the position of the articulation is more or less that shown in FIG. 3a. As the contracture dissolves and the biological remodeling of the tissues takes place, the pseudo-elastic spring 12 is gradually brought towards the more extended position shown in FIG. 3b. The instantaneous angular position is given by the balance between the muscular forces and the corrective thrust of the spring: although the general trend during the therapy is from a flexed position (FIG. 3a) to an extended position (FIG. 3b), variations are possible, due to the changing conditions of the patient. The orthosis with pseudo-elastic joints allows these oscillations, but tends towards extension as soon as possible.

Figure 4:
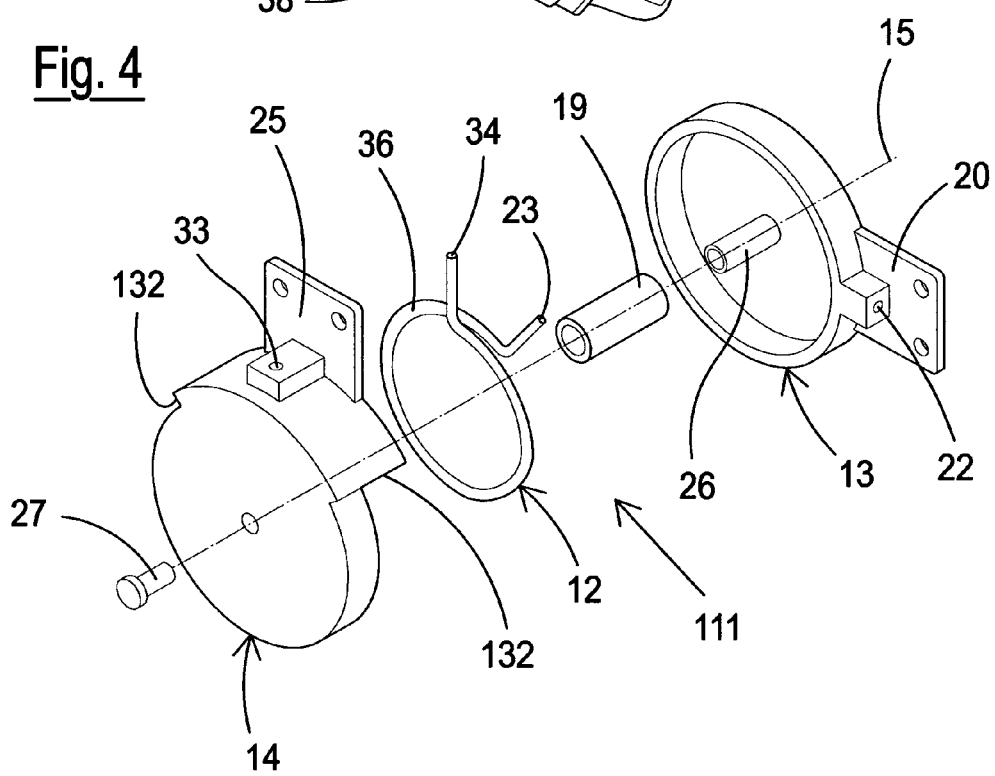
FIG. 4 is an exploded schematic perspective view of a further embodiment of a joint according to the present invention.

In the further embodiment of FIG. 4, equal elements are indicated with the same reference numbers or preceded by a "1". In this example, the overall structure of the joint 111 is simplified as the second box-shaped element 14 consists of a single piece and is provided with a double shaped stop-surface 132 which collaborates with the arm 20 of the first box-shaped element 13 as run-end. For this purpose, the double shaped stop-surface 132 is symmetrical on the second box-shaped element 14 with respect to a central axis and the relative arm 25 is positioned centrally with respect to this central axis. In this way, it can be assembled on both sides of the articulation keeping the encumbrance of the joint completely external.

Figure 5A:
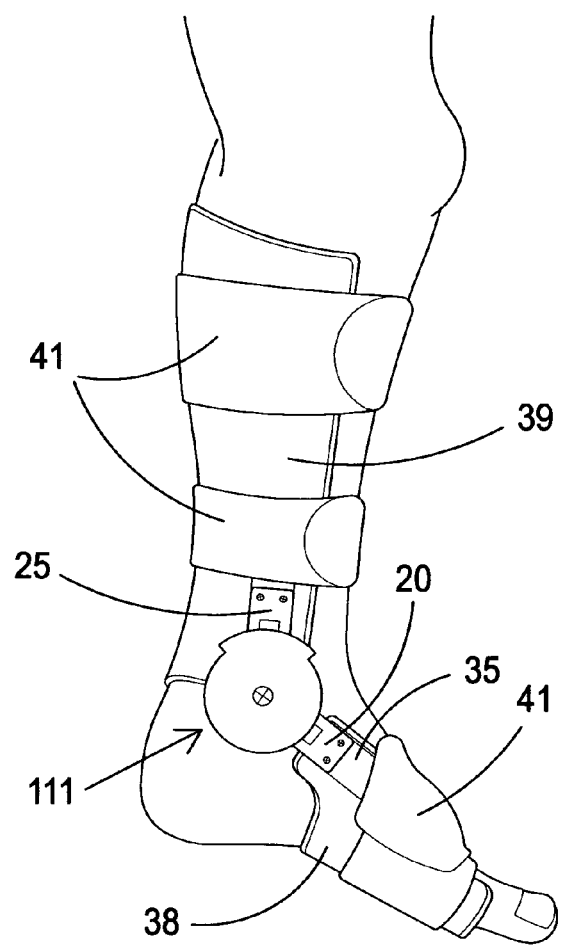
FIGS. 5a and 5b are schematic perspective views which illustrate the use of a pair of joints of FIG. 4 applied to an orthesis for the ankle in two different moments.
Figure 5B:
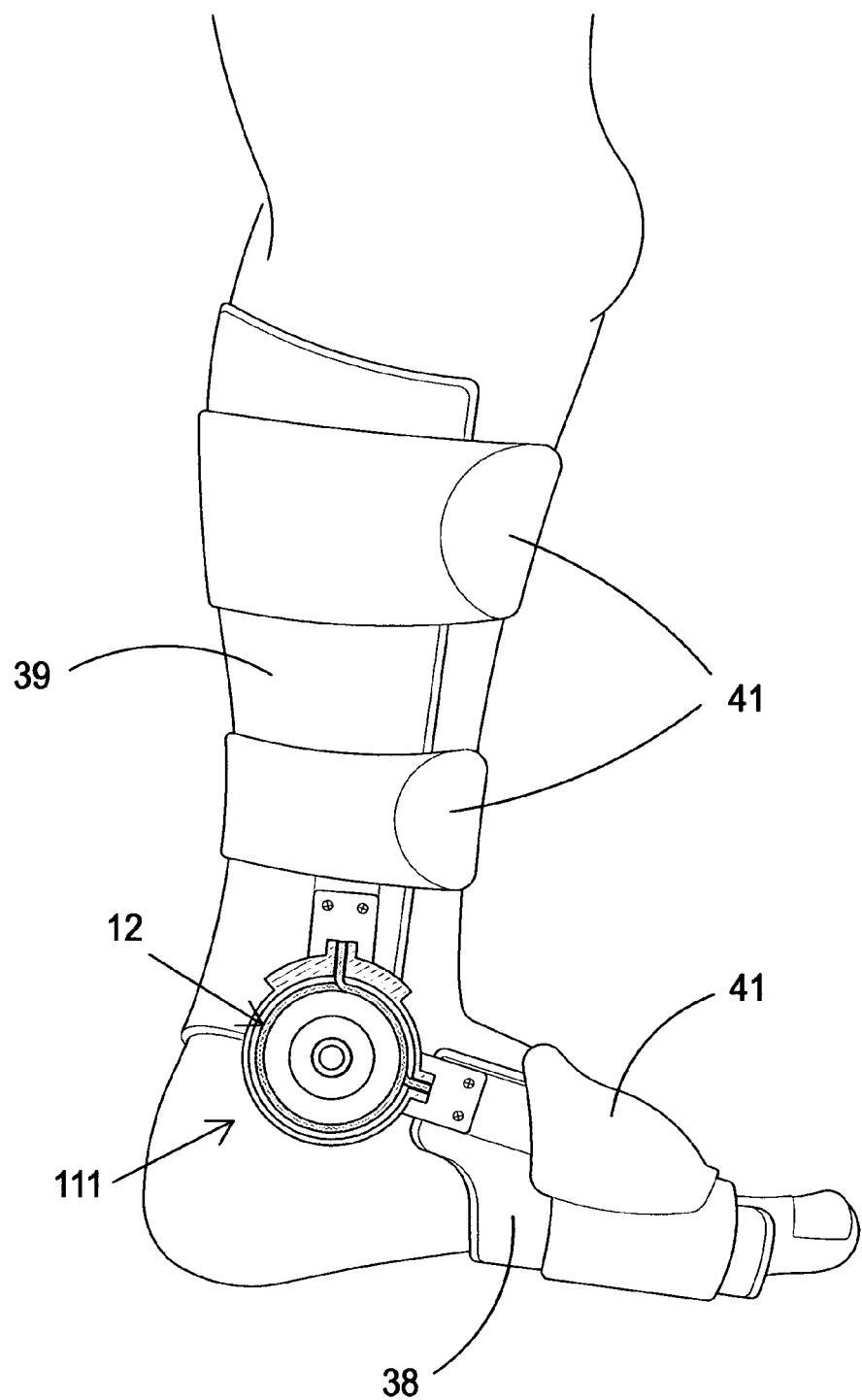

FIGS. 5a and 5b show how two joints 111 (of which only one is shown) are positioned in an orthosis for the ankle.

The spring 12 tends to bring the contracted ankle in plane flexion (FIG. 5a) towards a more dorsiflexion position (FIG. 5b).

Voluntary movement is not prevented and consequently an orthosis of this kind can be used for correcting the gait in walking patients.

It can therefore be understood how the main field of application of the joint of the invention is consequently physical rehabilitation. The maximum advantages are in fact obtained in subjects who have undergone neurological injury with the development of contractures and spasticity of the muscles which affect one or more articulations of the limbs. The orthosis with pseudo-elastic joints of the invention is consequently applied with excellent results in:
1. gradually repositioning the articulation, without preventing voluntary or involuntary movements in any way, due to the activation of the muscles to be treated or their antagonists;
2. favouring the remodeling and elongation of contracted or spastic muscles normally maintaining them in an extended position.

Furthermore, the same joint can be used for preventive purposes, i.e. for preventing the development of spasticity or contractures during a paresis or together with other therapies, comprising but not limited to pharmacological denervation therapies or other forms of physiotherapy.

Other applications already envisaged for the joint proposed are in functional ortheses, i.e. which help a patient exert a specific function, typically but not exclusively, walking. The joint in fact guarantees total freedom of movement as it exerts a force which moves the equilibrium of the forces during the active movement cycle. In the case of an ankle, the pseudo-elastic joint can be useful for helping weak dorsiflexion muscles (in the case of drop-foot) or for opposing spastic plane flexions (in the case of clubfoot). Unlike other elastic means already proposed in known applications (for example U.S. Pat. No. 6,824,523), the hysteretic behaviour provided by the pseudo-elastic material allows the force level in favour of weak muscles (lower) to be differentiated from contrasting spastic muscles (higher). In this way, weaker muscles are in any case subjected to a stress level useful for their functional recovery.

Furthermore, the joints can also be used by non-neurological patients for analgesic positioning and by healthy subjects, for example for muscle strengthening, in which case they exercise the muscles against the force produced by the joints.

Further applications which lie outside the rehabilitative scope are in mechanical systems, comprising but not limited to robotic systems, in which the joint has the function of producing a position of equilibrium between hinged components.

There are many possible embodiments for a joint for articulations with pseudo-elastic elements according to the present invention. The minimum requisites which associate all possible embodiments are:
1. constraining the pseudo-elastic element contained therein, transferring the force it exerts to an orthosis or other elements which are associated with an orthosis;
2. maintaining the pseudo-elastic element pre-charged also at angular run-end;
3. limiting the encumbrance of the pseudo-elastic element when this is charged;
4. guaranteeing the patient's safety in the case of breakage of the pseudo-elastic element.

The two embodiments previously proposed satisfy these requisites.

It is therefore evident how the joint of the invention is based on the equilibrium of the forces in question.

The angle at which the articulation is positioned is in fact always determined by the balance between the force expressed instantaneously by the muscles and the resistance (almost constant) offered by the brace. The use of a pseudo-elastic material not only allows this equilibrium but in any case also favours movements towards the final desired position with respect to movements in a contrary direction. This is possible thanks to the presence of a mechanical hysteresis which is such as to raise the resistant force when the movement goes in a non-therapeutic direction.

In order to exploit this principle, the material must still be in the plateau area at the run-end of the orthosis, i.e. it must be subjected to a pre-charging which overcomes the initial linear elastic behaviour.

The objective indicated in the preamble of the description has therefore been achieved.

The forms of the structure for the embodiment of a joint according to the invention, as also the materials and assembly modes, can naturally differ from those shown for purely illustrative and non-limiting purposes in the drawings.

The protection scope is therefore delimited by the enclosed claims.

The invention claimed is:
1. A joint for articulations comprising:
a pair of coupled box-shaped elements, facing each other in an open surface, moveable and rotating with respect to each other, around a common longitudinal axis, a spring-charged pseudo-elastic element positioned within the pair of coupled box-shaped elements and including at least a curved portion substantially forming a ring and two straight portions terminating in a first end and a second end, said two straight portions including said first end and said second end developing radially in a plane substantially parallel to a lying plane of the curved portion; said first end being positioned in a hole in one of said pair of coupled box-shaped elements and said second end being positioned in another of said pair of box-shaped elements whereby said spring charged pseudo-elastic element causes the reciprocal rotation of each element of said pair of coupled box-shaped elements;

each of said pair of coupled box-shaped elements carrying an arm that faces outwardly for connection with associated portions of an articulation and including a stop element;

said joint further comprising an interposed ball bearing that is situated on or within inner extensions of said pair of coupled box-shaped elements, wherein said spring-charged pseudo-elastic element is positioned around said inner extensions;

said extensions carrying an axial constraint member for said pair of coupled box-shaped elements.

2. The joint for articulations according to claim 1, wherein an element of said pair of coupled box-shaped elements comprises said inner extension which is a sleeve, positioned on a base and centrally aligned with said common longitudinal axis of said pair of coupled box-shaped elements, said inner extension acting as an external housing for said interposed ball bearing, and the other inner extension being a pin which acts as an inner seat for said interposed bearing.

3. The joint for articulations according to claim 1, wherein said straight portions of the spring-charged pseudo-elastic element are intersected to obtain a pre-charge before being inserted into the holes.

4. The joint for articulations according to claim 1, wherein said stop elements of said pair of coupled box-shaped elements comprise shaped stop-surfaces which extend radially towards the outside from one box-shaped element and axially towards the other box-shaped element.

5. The joint for articulations according to claim 1, wherein one of said pair of coupled box-shaped elements comprises a circular plate equipped with said arm facing outwardly for connection with associated portions of an articulation, an annular circular element constrained to the circular plate by screws, said circular plate and said annular circular element comprising holes in such a number as to allow fixing in at least two different reciprocal positions.

6. The joint for articulations according to claim 1, wherein, on a first one of said pair of coupled box-shaped elements, the stop element includes at least one shaped stop-surface which extends radially towards the outside from and axially towards a second one of said pair of coupled box-shaped elements; and wherein, on a second one of said pair of coupled box-shaped elements the stop element is defined by said arm.

7. The joint for articulations according to claim 1, wherein the axial constraint member includes a threaded fastener.

8. The joint for articulations according to claim 1, wherein the axial constraint member includes an axially extending body and a head radially extending beyond the body.

9. A joint for articulations comprising:

a pair of coupled box-shaped elements, facing each other in an open surface, moveable and rotating with respect to each other, around a common longitudinal axis, each of the pair of coupled box-shaped element containing a spring-charged pseudo-elastic element terminating in a first end and a second end; said first end being positioned in a hole in one of said pair of coupled box-shaped elements and said second end being positioned in another of said pair off box-shaped elements whereby said spring charged pseudo-elastic element causes the reciprocal rotation of each element of said pair of coupled box-shaped elements;

each element of said pair of coupled box-shaped elements carrying an arm that faces outwardly for connection with associated portions of an articulation and including at least a stop element;

said joint further comprising an interposed ball bearing that is situated on or within inner extensions of said pair of coupled box-shaped elements, wherein said spring-charged pseudo-elastic element is positioned around said inner extensions;

said extensions carrying an axial constraint member for said pair of coupled box-shaped elements;

wherein said inner extensions of said pair of coupled box-shaped elements comprises a sleeve and a pin interpenetrating one another and positioned respectively on a base of the relative element of said pair of coupled box-shaped elements; said pin and said sleeve being aligned with a said common longitudinal axis so that the sleeve acts as an external housing for said interposed ball bearing, and said pin is inserted in said interposed ball bearing.

10. The joint for articulations according to claim 9, wherein the axial constraint member includes a threaded fastener.

11. The joint for articulations according to claim 10, wherein the axial constraint member includes an axially extending body and a head radially extending beyond the body.

* * * * *